United States Patent [19]

Glaberson

[11] Patent Number: 4,938,764
[45] Date of Patent: Jul. 3, 1990

[54] TICK REMOVER

[76] Inventor: John Glaberson, 99 Alberts Hill Rd., Newtown, Conn. 06470

[21] Appl. No.: 360,778

[22] Filed: Jun. 2, 1989

[51] Int. Cl.⁵ .................. A61B 17/00; A01M 3/00
[52] U.S. Cl. ................................... 606/131; 254/18
[58] Field of Search .......................... 606/205–207, 606/210, 211, 131, 138; 254/18

[56] References Cited

U.S. PATENT DOCUMENTS

| | | | |
|---|---|---|---|
| 1,615,125 | 1/1927 | Lespinasse | 606/207 X |
| 2,569,237 | 9/1951 | Hall | 606/161 |
| 4,213,460 | 7/1980 | Weiner | 606/205 X |
| 4,442,837 | 4/1984 | Keatley | 606/131 |

Primary Examiner—Mickey Yu
Attorney, Agent, or Firm—Haynes N. Johnson

[57] ABSTRACT

A tick remover for removing ticks for the skin of a man or an animal including an elongated handle, a wire loop formed integrally with the handle at one end the wire loop including a opening proximate to the handle which is large enough to receive the body of a the tick and a contiguous opening removed from the handle which is large enough to receive the neck of the tick but not large enough to receive the body of the tick, so that the contiguous opening may be fitted about the neck of the tick and the tick's head pulled from the skin.

7 Claims, 1 Drawing Sheet

TICK REMOVER

FIELD OF THE INVENTION

This invention relates to the field of tick removers and particularly to ones which readily remove ticks from animals and humans.

BACKGROUND OF THE INVENTION

The removal of engorged, or partially engorged, ticks from the skin of man and animals has always been a problem. It has become even more serious with the onset of Lyme disease. Efforts to remove ticks from the skin have involved using tweezers or some other form of pincers and of applying liquids or hot objects in an attempt to cause the tick to disengage voluntarily. These methods are difficult and often fail, and sometimes they leave a portion of the tick in the skin, which may lead to infection. By contrast, my device is simple and effective.

BRIEF SUMMARY OF THE INVENTION

My invention involves a thin, molded plastic handle having an especially shaped wire loop extending from one end, the loop having been molded into the handle. The loop has two portions. The first is an inner portion, adjacent to the handle and large enough to fit about the body of the engorged tick. The second is an outer U-shaped portion integral with the first, and extending the loop outwardly from the inner portion; it has an inner width less than the width of the tick's body but wide enough to go about its neck. For convenience, it may be at a slight angle to the inner loop.

In use, the inner loop is put over the tick's body so that the U-shaped portion fits about the neck. Then, with a gentle pull, the tick's head may be removed from the skin.

DETAILED DESCRIPTION OF THE INVENTION

My tick remover 1 is made of a molded plastic handle 3 integrally molded to the ends of a wire so as to form a loop 9. The handle may have holes 5 in it to provide for a surer grip.

Figure 1:
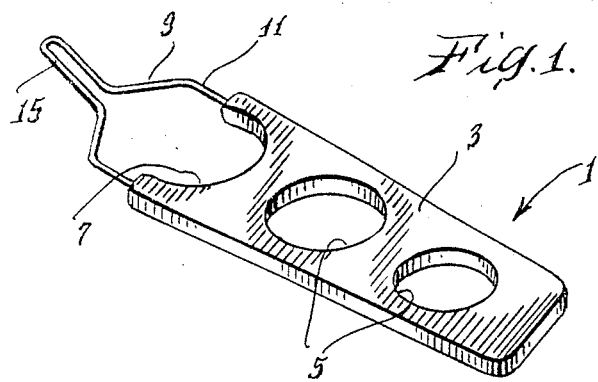
FIG. 1 is a perspective view of my tick remover.
Figure 2:
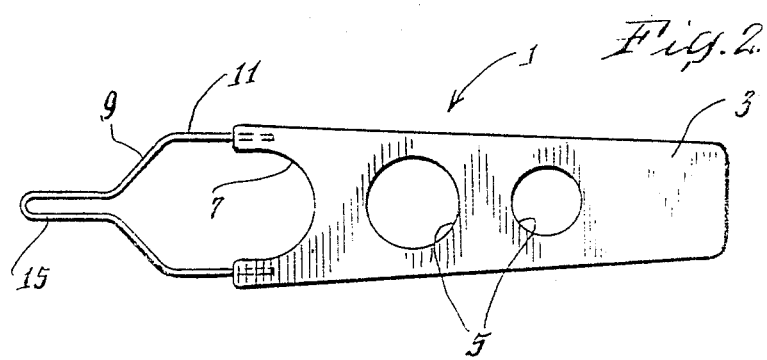
FIG. 2 is a plan view thereof.
Figure 3:
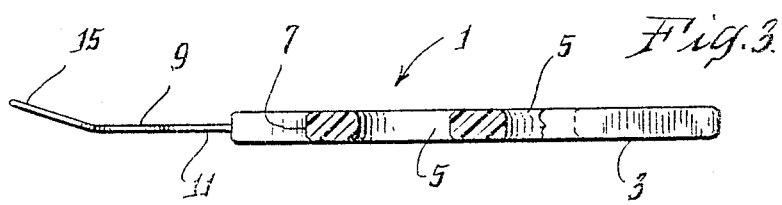
FIG. 3 is a side elevation.

Loop 9 is formed of three parts, a curved area 7 at the end of handle 3, an inner loop portion 11, and an outer, U-shaped portion 15 extending away from the handle. The inner loop 11 with curved area 7 provide a large enough diameter to receive the body of an engorged tick. Outer portion 15 has a width which is large enough to receive the neck of the tick, but too narrow to let the body through. The device is easier to use if the outer portion 15 is angled with respect to the inner loop 11, as shown in FIG. 3. Loop portions 11 and 15 are made of semi-stiff wire such as that found in a standard No. 1 paper clip.

It is preferable that loop 9 be a closed loop. In this way it will not get snarled in use, such as getting caught in a dog's hair.

I have found the following dimensions to work well: inner diameter of inner loop 0.70"; inner width of U-shaped outer portion 0.03"; length of outer portion 0.45"; wire diameter 0.024"; length of handle 2.5"; and thickness of handle 0.15".

Figure 4:
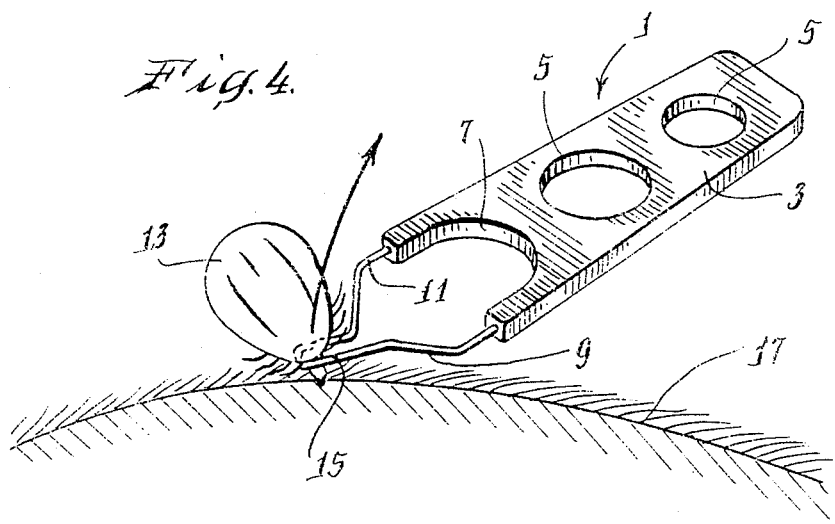
FIG. 4 is a view showing the tick remover being used to remove a tick from the skin.

In use the loop 11 of the tick remover 1 is placed around the body of the tick 13 and the unit moved so that outer loop 15 fits about the tick's neck (See FIG. 4). By pulling the remover in a direction away from the skin 17, the head is pulled out of the skin and the tick removed.

If desired, loop portions 11 and 15 can be molded integrally with the handle 3, and of the same material as the handle, instead of being made of wire. This could effect economy in manufacture and, so, permit it to be disposed of after a single use, without removing the tick from the loop.

I claim:

1. A tick remover for removing ticks from the skin, said tick remover including
    a molded plastic handle and a fixed loop integral with said handle,
    said loop together with the end of said handle forming an inner loop portion and an outer U-shaped portion removed from said handle, said inner loop portion being large enough to permit the passage of the body of an engorged said tick, and said outer U-shaped portion being wide enough to permit the passage of the neck of said tick, but not so wide as to permit the passage of the body of said tick,
    whereby said U-shaped portion may be fitted about the neck of said tick and said tick pulled from said skin.

2. A tick remover as set forth in claim 1 in which said U-shaped portion is at an angle to said inner loop portion.

3. A tick remover as set forth in claim 1 in which said loop is a wire embedded in said handle.

4. A tick remover as set forth in claim 1 in which said handle has at least one hole therethrough to provide for better gripping of said handle.

5. A tick remover as set forth in claim 1 in which said loop and said handle form a closed circuit.

6. A tick remover for removing ticks from the skin of a man or an animal, said tick remover including
    an elongated handle, a fixed loop formed integrally with said handle at one end thereof, said loop including an opening proximate to said handle which is large enough to receive the body of a said tick and a contiguous opening removed from said handle which is large enough too receive the neck of said tick but not large enough to receive the body of said tick,
    whereby said contiguous opening may be fitted about the neck of said tick and said tick's head pulled from the skin.

7. A tick remover as set forth in claim 6 in which said loop is wire.

* * * * *